US011636953B2

United States Patent
Dorn

(10) Patent No.: US 11,636,953 B2
(45) Date of Patent: Apr. 25, 2023

(54) METHOD FOR COMPARING REFERENCE VALUES IN MEDICAL IMAGING PROCESSES, SYSTEM COMPRISING A LOCAL MEDICAL IMAGING DEVICE, COMPUTER PROGRAM PRODUCT AND COMPUTER-READABLE PROGRAM

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 786 days.

(21) Appl. No.: 16/114,617

(22) Filed: Aug. 28, 2018

(65) Prior Publication Data
US 2019/0066848 A1    Feb. 28, 2019

(30) Foreign Application Priority Data
Aug. 31, 2017    (EP) .................................... 17188845

(51) Int. Cl.
*G16H 15/00* (2018.01)
*G16H 50/70* (2018.01)
(Continued)

(52) U.S. Cl.
CPC .......... *G16H 50/70* (2018.01); *G06F 16/285* (2019.01); *G16H 10/60* (2018.01); *G16H 15/00* (2018.01);
(Continued)

(58) Field of Classification Search
CPC ............................................... G06Q 50/22–24
See application file for complete search history.

(56) References Cited

U.S. PATENT DOCUMENTS 6,272,469 B1 *   8/2001   Koritzinsky ............. A61B 6/56
                                                            705/2
2003/0179917 A1   9/2003   Faber et al.
(Continued)

FOREIGN PATENT DOCUMENTS

CN   1447284 A   10/2003
CN   1971565 A   5/2007
(Continued)

OTHER PUBLICATIONS

"Mapping Radiology Orders to RadLex"; Treena Hansen; Jan. 3, 2017; 3M HDD Access (Year: 2017).*
(Continued)

*Primary Examiner* — John A Pauls
(74) *Attorney, Agent, or Firm* — Harness, Dickey & Pierce, P.L.C.

(57) ABSTRACT

A method is for comparing reference values in medical imaging processes of different medical imaging devices. In an embodiment, the method includes providing a data base of reference values, each reference value of the data base being assigned to a defined global identification specifying the medical imaging process; creating a label for the medical imaging process at a local medical imaging device using the defined global identification; and providing a mapping assigning a local identification to the defined global identification, for supporting the creation of the label for the medical imaging process.

29 Claims, 2 Drawing Sheets

(51) Int. Cl.
    *G16H 10/60*     (2018.01)
    *G06F 16/28*     (2019.01)
    *A61B 6/03*     (2006.01)
    *G16H 40/60*     (2018.01)
    *G16H 50/50*     (2018.01)
    *G16H 30/20*     (2018.01)
    *G16H 40/20*     (2018.01)

(52) U.S. Cl.
    CPC .............. *A61B 6/032* (2013.01); *G16H 30/20* (2018.01); *G16H 40/20* (2018.01); *G16H 40/60* (2018.01); *G16H 50/50* (2018.01)

(56) References Cited

U.S. PATENT DOCUMENTS

| | | | |
|---|---|---|---|
| 2007/0081700 A1 | 4/2007 | Blumenfeld et al. | |
| 2010/0239069 A1* | 9/2010 | Bourdeaux | A61B 6/56 378/96 |
| 2011/0301457 A1 | 12/2011 | Yoshiara et al. | |
| 2012/0106817 A1* | 5/2012 | Shih | A61B 6/583 382/131 |
| 2012/0128116 A1* | 5/2012 | Sabol | A61B 6/032 378/4 |
| 2012/0213326 A1* | 8/2012 | Walker | G06F 19/00 378/4 |
| 2012/0246181 A1 | 9/2012 | Nowinski et al. | |
| 2014/0010428 A1 | 1/2014 | Schmidt | |
| 2015/0356258 A1 | 12/2015 | Moore | |
| 2019/0180145 A1 | 6/2019 | Chen et al. | |

FOREIGN PATENT DOCUMENTS

| | | |
|---|---|---|
| CN | 102274046 A | 12/2011 |
| CN | 103536360 A | 1/2014 |
| CN | 106530236 A | 3/2017 |
| CN | 106682435 A | 5/2017 |
| CN | 107025369 A | 8/2017 |
| WO | WO 2014116926 A1 | 7/2014 |

OTHER PUBLICATIONS

Radiological Society of North America (RSNA) website—Data Tools and standards—RadLex radiology lexicon (Year: 2021).*
DICOM Correction item CP 751 (Year: 2007).*
"Targeted CT Dose Reduction Using a Novel Dose Metric and the American College of radiology Dose Index registry: Application to Thoracic CY Angiography"; Zamora et al.; Nov. 2016 (Year: 2016).*
"Dose Monitoring in Radiology Departments: Status Quo and Future Perspectives"; Boos et al.; 2016 (Year: 2016).*
"Implementation of the ACR Dose Index Registry at a Large Academic Institution: Early Experience"; Robinson et al.; Nov. 14, 2012 (Year: 2012).*
"Comparison of effective radiation doses from X-ray, CT, and PET/CT in pediatric patients with neuroblastoma using a dose monitoring program"; Kim et al. Jul. 14, 2016; Diagnostic and Interventional Radiology. (Year: 2016).*
Nema.org website printout—DICOM RDSR Template; Jun. 11, 2017. Recovered from the Internet Archive on Feb. 10, 2022. (Year: 2017).*
"Mapping Institution-Specific Study Descriptions to RadLex Playbook Entries"; Mabotuwana et al.: Jan. 15, 2014. (Year: 2014).*
"Benchmarking Radiation Dose Indices: The American College of Radiology's Dose Index Registry" by Laura Coombs (2013) (Year: 2013).*
ACR DIR Mapping Tool User Guide; 2011 (Year: 2011).*
Singh S. et al.: "Standardized CT protocols and nomenclature: better, but not yet there"; in: Pediatric Radiology (Springer-Verlag); vol. 44, No. 3; pp. 440-443; Oct. 11, 2014.
Morin R. L. et al.: "ACR Dose Index Registry"; in: Journal of the American College of Radiology; vol. 8; No. 4; pp. 288-291; Mar. 1, 2011; ISSN: 1546-1440.
Cook T. S. et al.: "Automated Extraction of Radiation Dose Information for CT Examinations"; in: Journal of the American College of Radiology; vol. 7; No. 11; pp. 871-877; Nov. 1, 2010.
Silva L. A. et al.: "Normalizing Heterogeneous Medical Imaging Data to Measure the Impact of Radiation Dose"; in: Journal of Digital Imaging (Springer-Verlag); vol. 28; No. 6; pp. 671-683; May 27, 2015; ISSN: 0897-1889.
Extended European Search Report dated Jan. 4, 2018.
European Office Action dated Jan. 27, 2020.
European Intention to Grant dated Oct. 30, 2020.
Chinese Office Action dated May 14, 2021, for corresponding Chinese Patent Application No. 201811016565.3 and English translation.

* cited by examiner

METHOD FOR COMPARING REFERENCE VALUES IN MEDICAL IMAGING PROCESSES, SYSTEM COMPRISING A LOCAL MEDICAL IMAGING DEVICE, COMPUTER PROGRAM PRODUCT AND COMPUTER-READABLE PROGRAM

PRIORITY STATEMENT

The present application hereby claims priority under 35 U.S.C. § 119 to European patent application number EP17188845.6 filed Aug. 31, 2017, the entire contents of which are hereby incorporated herein by reference.

FIELD

At least one embodiment of the present invention describes a method for comparing reference values in medical imaging processes, a system comprising a local medical imaging device, a computer program product and/or a computer-readable program.

BACKGROUND

Medical imaging devices, such as computer tomography (CT)-scanner, nuclear medicine (NM)-scanner, positron emission tomography (PET)-scanner, X-ray-scanner (XA), fluoroscopy (RF)-scanner, mammography (MG)-scanner, typically use radiation, in particular X-ray radiation, for recording a medical image. For example the radiation dose used for recording the medical image is a crucial technical parameter, since a radiation dose being too large can cause damages to a patient. Therefore, reference values exist that represents critical thresholds.

SUMMARY

The inventors, however, have recognized that the reference value being used at different local medical imaging devices might distinguish from each other, because the medical imaging devices are from different vendors and/or the reference value being used depends on the modality of the radiation process. Due to the different individual local identifications for labelling of the medical images at each local medical imaging device it cannot guaranteed that the used reference values of different local medical instruments are comparable with each other.

At least one embodiment of the present invention provides a method for comparing reference values in medical imaging processes of different local medical imaging devices, although the medical imaging devices use their own local identification.

Embodiments of the present invention are directed to a method for comparing reference values in medical imaging processes; a system; a computer program product and/or a computer readable computer medium.

According to a first embodiment of the present invention a method for comparing reference values in medical imaging processes of different medical imaging devices, in particular for establishing a fundament for comparing reference values in medical imaging processes of different medical imaging devices, is provided, comprising:

providing a data base of reference values, wherein each reference value of the data base is assigned to a defined global identification specifying the medical imaging process, in particular specifying a medical imaging protocol for the medical imaging process, for example for each medical imaging device, i.e. modality;
creating a label, such as specific name or number for example, for the medical imaging process at a local medical imaging device and/or a local workstation, in particular a workstation related to the local medical imaging device, by using the defined global identification for specifying the medical imaging process; and
providing a mapping that assigns a local identification to the defined global identification for supporting the creation of the label for the medical imaging process, wherein the data base is available to several spatial separated local medical imaging devices, in particular to local medical imaging devices at different hospitals.

In at least one embodiment, it is provided that a benchmarking data set, in particular a benchmarking data set of the reference values, is created for a subset of local medical imaging devices, in particular by a benchmarking module, comprising assigning a classification value to the subset of medical imaging device, in particular assigning a classification value to a subset of hospitals assigned the medical imaging device; and
creating a benchmarking data set based on the classification value. Preferably, the created benchmarking data set is assigned to the global identification.

Another embodiment of the present invention is directed to a system comprising a local medical imaging device, wherein the system is configured for providing a data base of reference values, wherein each reference value of the data base is assigned to a defined global identification specifying the medical imaging process;
creating a label for the medical imaging process at a local medical imaging device and/or a local workstation, in particular a workstation related to the local medical imaging device, by using the defined global identification for specifying the medical imaging process; and
providing a mapping that assigns a local identification to the defined global identification for supporting the creation of the label for the medical imaging process. Preferably, the system comprises at least a control unit having a processor that is configured for executing one of the steps of the method according to the invention.

A further embodiment of the present invention is directed to a non-transitory computer program product comprising program elements for carrying out the steps of the method according to at least one embodiment of the present invention, when the program elements are loaded into a memory of a programmable device.

A further embodiment of the present invention is directed to a non-transitory computer-readable medium on which is stored a program elements that can be read and executed by a computer unit in order to perform steps of the method according to at least one embodiment of the present invention when the program elements are executed. The computer-readable medium may be a data carrier such as the cloud, a hard disc, CD-ROM, SD-card or other digital medium. The computer unit and the programmable device may be any form of digital calculating device, e.g. a PC, smart phone, tablet computer, cloud, workstation or handheld device. Preferably, the computer unit and/or the programmable device are incorporated into the system described above, in particular into the control unit.

DETAILED DESCRIPTION OF THE EXAMPLE EMBODIMENTS

Figure 1:
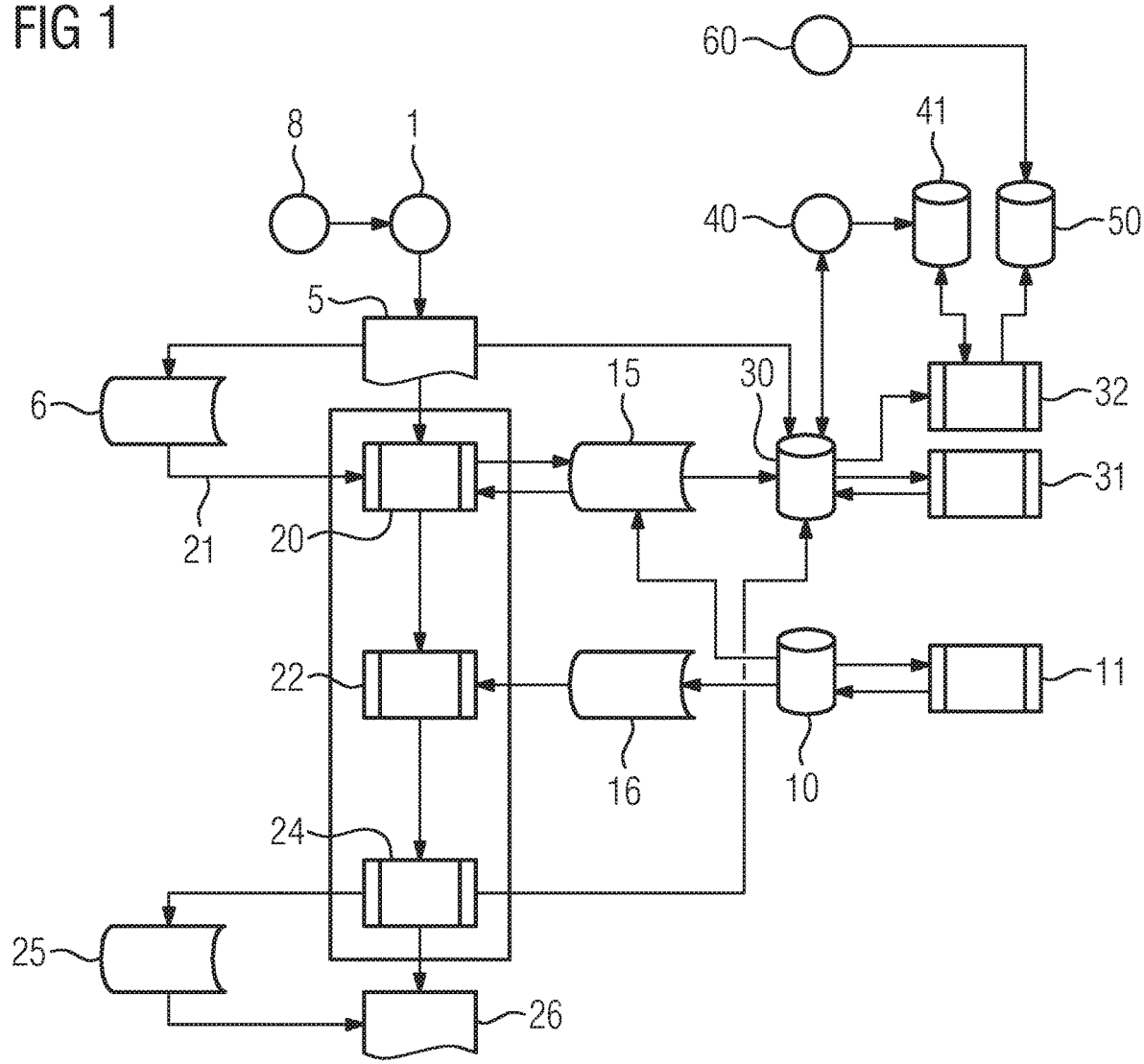
FIG. 1 shows a flow diagram illustrating a method of an embodiment of the invention, for comparing reference values in medical imaging processes of different medical imaging devices at a local medical imaging device, in particular at a local medical imaging device located at a hospital

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, a method is provided, for comparing reference values in medical imaging processes of different medical imaging devices, in particular for establishing a fundament for comparing reference values in medical imaging processes of different medical imaging devices, comprising:

providing a data base of reference values, wherein each reference value of the data base is assigned to a defined global identification specifying the medical imaging process, in particular specifying a medical imaging protocol for the medical imaging process, for example for each medical imaging device, i.e. modality;

creating a label, such as specific name or number for example, for the medical imaging process at a local medical imaging device and/or a local workstation, in particular a workstation related to the local medical imaging device, by using the defined global identification for specifying the medical imaging process; and providing a mapping that assigns a local identification to the defined global identification for supporting the creation of the label for the medical imaging process, wherein the data base is available to several spatial separated local medical imaging devices, in particular to local medical imaging devices at different hospitals.

Contrary to that known, a mapping is provided, wherein the mapping correlates the individual local identification and the global defined identification, in particular at the individual local medical imaging device. Thus, it is advantageously possible to use a common set of global identifications for specifying each medical imaging process or type of medical imaging process.

As a consequence, a plurality of medical imaging devices being located at different hospitals can specify medical images by referring to a common reference value that is assigned to the respective global identification. In particular, it is possible to compare the medical imaging processes although the different local medical imaging devices use different local identifications. Thereby, the mapping supports the creation of the label in a proper form for comparing, i. e. in a form using the global identification.

Furthermore, using the global identification allows establishing a benchmarking of reference values by referring specific reference values to the global identification. Moreover, it is thinkable that the label is created by an operator and or a workstation, such as a computer, being configured for replacing the local identification by the global identification. Preferably, the data base is included into a server, for example in a network or a cloud, and forms a register for reference values. Thus, several different hospitals can access to one common server, one common server system having several server and/or a common cloud.

Preferably, the term "local medical imaging device" describes a specific medical imaging device, such as a nuclear medicine (NM)-scanner, a positron emission tomography (PET)-scanner, X-ray-scanner (XA), fluoroscopy (RF)-scanner, mammography (MG)-scanner, located at a defined spot. Preferably, the term "local workstation" can also refer to a (personal) computer, a virtual machine running on host hardware, a microcontroller, or an integrated circuit. As an alternative, the local workstation can be a real or a virtual group of computers (the technical term for a real group of computers is "cluster", the technical term for a virtual group of computers is "cloud"). Preferably, the local workstation comprises a calculation unit and a memory unit.

A calculation unit can comprise hardware elements and software elements, for example a microprocessor or a field programmable gate array. A memory unit can be embodied as non-permanent main memory (e.g. random access memory) or as permanent mass storage (e.g. hard disk, USB stick, SD card, solid state disk). The local workstation can be part of the local medical imaging device.

In particular, the local medical imaging device represents a specific medical imaging device located at a specific hospital or institution. That means the "local medical imaging device" and the "local workstation" represent an individual medical imaging device and/or an individual local workstation. Due to a setting incorporated into the medical imaging device by the producer of the medical imaging device and/or due to guidelines established in the hospital and/or country each of the local medical imaging devices can use or create a different local identification for labelling the same medical imaging process by their own. The result is a not-unified labelling by using the respective local identification, since each hospital, workstation and/or medical imaging device uses a different local identification for labelling the same or comparable medical imaging process. In other words: the labelling of the medical imaging process is managed locally and therefore the local identifications differ from each other from medical imaging device to medical imaging device and/or form hospital to hospital.

In general, the term "medical imaging process" represents a collective term for recording a medical imaging data set by using the specific medical imaging device. The medical imaging process is specified for example by the type of the medical imaging device, a body region being examined, a time of recording the medical imaging device and/or parameters and/or configurations of the medical imaging device. Preferably, the medical imaging process is performed based on a medical imaging protocol comprising the parameters for configuring the medical imaging device and the local identification represents the labelling for the specific medical imaging protocol at the specific medical imaging device and/or hospital.

In particular, the term "reference value" preferably comprises a magnitude of the radiation and/or a duration of the radiation. Preferably, the reference value comprises a scan-/exam-radiation-dose value, a scan-/exam-duration value and/or an image quality optimized-scan-/exam-radiation-dose value. It is also thinkable that reference value comprises the acquisition duration used by a magnetic resonance scanner or an ultrasound scanner. In particular, it is provided that the duration, such as the acquisition duration, is a benchmark category, when the benchmark category is not the magnitude of the radiation.

Preferably, the data base is configured such that for each possible modality and body region a reference value is provided. Preferably, the term "mapping" means that a link, in particular an individual link, is established between the local identification and the global identification.

Preferably, the set of global identifications represents a set of standard-modalities, in particular all available or realizable modalities, specified to a body part, in particular an inner body part. Thus, it is possible to establish reference values for each modalities and each body region. As a result, comparing is simplified, since the compared reference values are correlated to comparable modalities and it is possible to establish reference values for each modality.

Preferably, the term modality is a generic term for the specific medical imaging device used for exposing the patient to radiation. In particular, the global identification includes information about the medical device, the modality and/or the body part being exposed to the radiation.

Preferably, the global identification is represented by a Radlex-standard. According to the Radlex-standard each label name, such as XA abdominal aorta, is identified by a RPID, such as RPID 6195 for instance. Thus, the modality, such as using a X-ray (XA), and the body region or the body part, such as abdominal aorta, can be extracted directly from the label name or indirectly by the RPID.

Preferably, only the RPID, the label name, the modality and the body region are used. As a consequence, the method is not restricted to value management relevant modalities. For example, the medical imaging device is a computer tomography (CT)-scanner, a nuclear medicine (NM) scanner, positron emission tomography (PET)-scanner, a X-ray-scanner, a fluoroscopy (RF)-scanner, a mammography (MG) scanner, a x-ray-system, a angiography (XA) scanner, magnetic resonance tomography (MRT) scanner or an ultrasound (US) scanner.

In particular, a key performance indicator (KPI) is provided, wherein the KPI depends on the modality, and the reference values are assigned to these KPI. For CT values for SSDE (size-specific dose estimates)-Max, DLP (dose length product)-Max, CTDIVOL (computed tomography dose index volume)-Max (per scan and/or maximal values in the exam) represent KPIs, as well as a DLP-Acc and an EFF (effective) Dose (on exam level). Furthermore, a phantom size represents a CT relevant KPI (all reference values should be defaulted to a Body 32 phantom and it should be paid attention for events with mixed phantom types). KPI for MG are the values for RP (Reference Point)-Max, AGD (Average Glandular Dose)-Max (per scan and/or maximal values in the exam), AGD-Acc and Eff-Dose (on exam level). For XA, RF, XR and RP the values for RP-Max, DAP (dose-area product)-Max (per scan and/or maximal values in the exam), DAP-Acc and Eff-Dose (on exam level) are the corresponding KPIs. Finally, MBq (MegaBecquerel) and Eff-Dose (on exam level) represent the KPIs for NM and PET.

In general, the order of the method steps chosen for the description of the method does not imply that these method steps are in fact executed in this order. In particular, the steps of the presented methods can be executed in any order. In particular, the step of providing a mapping can be executed before the step of creating a label.

Particularly advantageous embodiments and features of the invention are given by the dependent claims as revealed in the following description. Features of different claim categories may be combined as appropriate to give further embodiments not described herein.

In at least one embodiment, it is provided that a benchmarking data set, in particular a benchmarking data set of the reference values, is created for a subset of local medical imaging devices, in particular by a benchmarking module, comprising assigning a classification value to the subset of medical imaging device, in particular assigning a classification value to a subset of hospitals assigned the medical imaging device; and creating a benchmarking data set based on the classification value. Preferably, the created benchmarking data set is assigned to the global identification.

An example for a classification value might be a type of hospital, such as a pediatric clinic, a multi-specialized hospital, an imaging center, a community hospital or an university hospital. Another classification value might be the area of the hospital. For example, the hospital is located in a rural area or metropolitan area. A further classification value might be a region, in which the hospital is located, such as for example a country, for instance Texas, and/or an orientation, for instance north, west, south, middle, east or the like (these classification values might relevant within the country the hospital is located). Thus, it is advantageously possible to create benchmark reference value sets of hospitals being comparable to each other and to compare hospitals of the same kind.

Preferably, an identifier for the hospital and the classification values are saved in a hospital data set, in particular at the data base. Preferably, the benchmarking data set comprises a min-value, a max-value, a 25%-value, a 75%-value, a mean value and/or a median value of the reference value, for example the radiation value and/or the radiation duration, for different classification values, preferably defined by the registration of the hospital.

Preferably, the benchmarking data set is created on demand or after a defined period of time, such as every month or every quarter. For example, the benchmarking data set is created interactively by using an application. Thus, the operator can choose a preferred classification value for comparing the radiation values of different hospitals having the same classification value. It is also thinkable that in a "period selection"-mode a pre-calculated benchmarking data set is provided by a background process, which runs once for every defined period of time to collect data from the data base, in particular from all available servers. Alternatively or additionally in a "Start-/End-Date selection"-mode it is possible to access online calculated benchmarking data sets, in particular calculated by the server or the cloud, provided on request from the data base to which the hospital and/or the medical imaging device is connected to.

Preferably the medical imaging device or an interface is configured for choosing between the "Start-/End-Date selection"-mode and "period selection"-mode. By creating the benchmarking data set it is advantageously possible that the operator, for example the hospital, relies on benchmarking data being already present at the data base. Consequently, time is saved and the pre-calculated benchmarking data set can be extended, i. e. updated, every month/quarter to add a new chunk of data being made available to the data base, i. e. to the server. In a preferred embodiment it is provided that the benchmarking data set is automatically created after a defined period of time, such as every month or every quarter, by the server or the system of server.

According to an example embodiment, it is provided that the mapping is provided by an auto-mapping mechanism or a manual mapping mechanism, in particular wherein the mapping is provided by the manual mapping mechanism, when the auto-mapping mechanism fails. By using the auto-mapping mechanism it is advantageously possible to establish a link between the local identification and the global identification. Thereby the auto-mapping mechanism preferably maps local identifications which are different across scanner models, vendors and/or institutions to the global identification. It is also thinkable that the mapping is performed semi-automatically, in particular in such cases in that a specific correlation between a local and a global identification fails in the auto-mapping mechanism.

Preferably, it is provided that the auto-mapping mechanism is performed by an artificial network, for example by a deep-learning mechanism. Thereby the artificial network for example analyses previous local identification and settings of the medical imaging device for assigning the local identification to the global identification.

Furthermore, it is provided that a duality matrix is realized for all relevant modalities for value relevant tags. In particular, the duality matrix supports the operator, when the global identification is established by the auto-mapping mechanism.

In particular, it is provided that in a preparation step an identifier, such as a hospital ID, is assigned to the local medical imaging device, in particular to the hospital of the local medical imaging device. For example, assigning the identifier to the local medical imaging device is included in registering the hospital for accessing the data base. Furthermore one or more classification values are assigned to the hospital during registration in the preparation step.

In another embodiment it is provided that the mapping that assigns the local identification to the defined global identification is visualized to an operator, in particular the global identification and the local identification are visualized simultaneously, and/or wherein the benchmarking data set is visualized to the operator, in particular in form of a boxplot, i.e. box and whisker plots are known from the stock market to display the variance of big data chunks in one picture. Thus, the operator is informed about the global identification and can correlate the global identification to the local identification being used by the operator in the past. In particular, a "standard-view-first"-mode is provided, wherein according to the "standard-view-first"-mode displaying the global identification is preferred to the local identification, in particular the local identification is replaced by the global identification automatically.

Alternatively or additionally, a "duality of view"-mode is provided, wherein according to the "duality of view"-mode the global identification and the local identification are displayed together. Thus, confusions by the operator can be avoided. In particular, the benchmarking data set for different classification values are presented next to each other for comparing the benchmarking data sets. Furthermore, it is thinkable that a global benchmarking data set, i. e. a teamplay boxplot, is displayed to show the evaluation in respect to the data being available at a server, in particular the cloud, without applying the classification value. Furthermore, it is possible to compare the benchmarking data to previous benchmarking data of the same modality. In particular, the benchmarking data set is provided together with the global identification, such as the RPID.

According to an example embodiment, it is provided that the global identification is included as information into a DICOM object. As a result, the auto-mapping mechanism, for example to the Radlex-standard, does not fail. In other word: the medical imaging device is configured such that the DICOM object is labelled with the global identification automatically by the medical imaging device. For example, the RPID is included to the DICOM-header. As a consequence, no manual mapping is needed, for any modality not just reference value relevant modalities.

Furthermore, it is provided that the global identification is incorporated into the medical imaging device, in particular such that the medical imaging device can use the incorporated global identification for labelling the medical imaging process. As consequence, it is advantageously possible to perform the labelling without mapping, in particular the auto-mapping mechanism.

Preferably, it is provided that the data base of reference values is stored on a server. Preferably, the server is part of a network or a cloud being available to several local medical imaging devices, in particular at different hospitals. Thus, the data base can be used by several local medical imaging devices together. Preferably, the reference values or reference durations are stored in a reference matrix being specified to the modality. The reference matrix is the final definition of a value register, which enables global reference value management, such for example time and/or dose or Exam-/scan-time management and benchmarking of reference values. The reference matrix includes the global identifications, in particular specifying the modality, and the reference values.

According to another embodiment, it is provided that an alarm is generated by an alert module, when the configuration value being used exceed the reference value. Thus the local medical imaging device can be informed about exceeding the reference value, for example by an alert notification, such as an email, to the tenant or operator. In particular, the alert notification includes the event and reference values used by the institution and/or in a network of several medical imaging device. Furthermore, the alert notification includes the national reference value. Preferably, the alert module is included into the local medical imaging devices.

In an example embodiment, it is provided that several references values are provided on basis of one reference values by a configuration module. Thus, several reference values and preferably categories and value/time units per modality can be extracted from one general reference values. For example, the general reference values is given for each modality and by using a k-value specified for each body region the specific reference values can be deduced from the general reference values. It is also thinkable that a correlation between reference values between different phantom types, such as a 16 cm or 32 cm phantom, and/or a correlation between the reference values of an adult and a pediatric are used for extracting the reference values from a general reference value.

Another embodiment of the present invention is directed to a system comprising a local medical imaging device, wherein the system is configured for providing a data base of reference values, wherein each reference value of the data base is assigned to a defined global identification specifying the medical imaging process;

creating a label for the medical imaging process at a local medical imaging device and/or a local workstation, in particular a workstation related to the local medical imaging device, by using the defined global identification for specifying the medical imaging process; and providing a mapping that assigns a local identification to the defined global identification for supporting the creation of the label for the medical imaging process. Preferably, the system comprises at least a control unit having a processor that is configured for executing one of the steps of the method according to the invention.

A further embodiment of the present invention is directed to a non-transitory computer program product comprising program elements for carrying out the steps of the method according to at least one embodiment of the present invention, when the program elements are loaded into a memory of a programmable device.

A further embodiment of the present invention is directed to a non-transitory computer-readable medium on which is stored a program elements that can be read and executed by a computer unit in order to perform steps of the method according to at least one embodiment of the present invention when the program elements are executed. The computer-readable medium may be a data carrier such as the cloud, a hard disc, CD-ROM, SD-card or other digital medium. The computer unit and the programmable device may be any form of digital calculating device, e.g. a PC, smart phone, tablet computer, cloud, workstation or handheld device. Preferably, the computer unit and/or the programmable device are incorporated into the system described above, in particular into the control unit.

In FIG. 1 a flow diagram illustrating a method of an embodiment for comparing reference values in medical imaging processes of different medical imaging devices 1 at a local medical imaging device, in particular at a local medical imaging device located at a hospital is presented. In particular, it is provided that the method establishes a fundament for comparing reference values 16 of radiation used for medical imaging although the medical imaging devices 1 might differ in respect to their location and their vendor and/or in the modality of using the reference values. For example, the medical imaging device 1 is a computer tomography (CT)-scanner, a nuclear medicine (NM)-scanner, positron emission tomography (PET)-scanner, a X-ray-scanner, a fluoroscopy (RF)-scanner, a mammography (MG)-scanner, a x-ray-system, a angiography (XA) scanner. Preferably, the reference value depends on a magnitude and/or a duration of radiation a patient is exposed to.

For realizing a comparison, a data base 10 is provided, wherein the data base 10 is configured such that a reference value 16 is assigned to a defined global identification 15 specifying the medical imaging process. Preferably, the data base 10 is incorporated into a server such as a cloud or a network and for example a reference value is provided for each global identification. In particular, a configuration module 11 is provided for configuring the data base 10 or for setting the reference values 16. It is also thinkable that the data base 10 includes a k-factor for each global identification, wherein the k-factor transforms the reference value to a reference value for a specific organ, in particular based on the formula:

$$REF(\text{ORGAN}) = k\text{-factor} \cdot REF(\text{MOD}),$$

wherein REF (ORGAN) corresponds to the reference value of the specific organ and REF (MOD) corresponds to the reference value stored at the data base for a modality and the REF (ORGAN) is set by the configuration module automatically.

Furthermore, it is provided that the several references values 16 are provided on basis of one reference value 16. In particular, an algorithm for evaluating the several reference values 16 is provided. In other words: the several reference values 16 can be extracted by using the algorithm. For example, the several reference values 16 form a sub-ensemble corresponding to the one reference value 16. For instance, the reference values are respectively correlated to a patient related information. The several reference values 16 correspond to the same modality but to an adult on one hand and to a pediatric on the other hand, for instance. Alternatively or additionally, the reference values 16 correspond to the same modality but to a 16 cm phantom ("head") on the one hand and to a 32 cm phantom ("body") on the other hand. Preferably, the algorithm is based on the formula $$REF(\text{``16 phantom''}) = 2 \cdot REF(\text{``32 phantom''}) \text{ and}$$

$$REF(\text{``Adult''}) = 2 \cdot REF(\text{``pediatric''}),$$

wherein REF ("16 phantom") corresponds to the reference value 16 of the 16 cm phantom, REF ("32 phantom") corresponds to the reference value of the 32 cm phantom, REF ("Adult") corresponds to the reference value 16 of the adult and REF ("pediatric") corresponds to the reference value 16 of the pediatric. As a consequence, it is possible to provide all four reference values 16 based on the reference values 16 of the 16 cm phantom of an adult, for instance by using the configuration module 11.

In particular, the defined global identification 15 includes
a label of modality for using the reference values 16, such as specifying the medical imaging device 1 as CT-scanner, and
a label of body region, such as aorta, chest, arteries for example. In particular, the global identification 15 includes a label. Thus, an individual reference value 16 can be assigned to each pair comprising modality and body region. Preferably, a Radlex standard description is used as global identification 15. Such a Radlex standard unambiguously correlates a label name, such as RPID6195, to a pair comprising a specific modality, such as angiography, and a body-region, such as an abdominal aorta. As a consequence, it is possible to directly extract from the global identification 15, i. e. the label name in the Radlex standard, the information about the modality and the body region of the medical imaging process. For comparing the reference values 16 of the different medical imaging devices it is intended that an operator at a local medical imaging device 1 uses the global identification 15 for labelling each medical imaging process. However, each operator and each medical uses an individual labelling, i. e. local identification.

For using the global identification 15 at the local medical imaging device 1 a mapping 21 between the local identification, i. e. the local label names, and the global identification 15 is provided, in particular by a mapping module 20. Thereby the global identifications 16 is provided to the medical imaging device 1, i. e. transferring the global identification 16 to the mapping module 20.

Furthermore, it is provided that an analysis 5 of the local identification is performed, for example by analysing the DICOM data. As a result relevant DICOM information 6 are extracted from the DICOM data and are transferred to the mapping module 20 for using the extracted DICOM information 6 as well as the results of analysing 5 the DICOM data for mapping 21. Preferably, the mapping 21 is performed automatically. It is also thinkable that an artificial network is used for mapping 21 the local identification to the global identification 15. Alternatively or additionally, it is provided that the mapping 21 is realized manually, i.e. the operator correlates the local identification to a global identification 15. For example, the manual mapping is performed for those global identifications 15 that could not correlated to a local identification automatically.

In order to support the operator labelling the medical imaging process it is preferably provided that the mapping 21 is visualized to the operator, for example on a screen. For example, an array or matrix including both the local identification and the correlated global identification 15 is presented. Thus, using the proper global identification is supported by the visualisation and the operator can select or choose the proper global identification 15. Furthermore, it is conceivable that the operator is informed about the change from using the local identification to the global identification 15 for the further proceeding.

It is also thinkable that the global identification 15 is incorporated into the medical imaging device 1, in particular the medical imaging device 1 is configured such that the DICOM objects generated by the specific medical imaging devices includes the global identification 15, such as the RADLEX-RPID. As a consequence, the mapping 21 using the DICOM data is simplified and the automatically mapping does not fail. In particular, it is possible to extract the RADLEX RPID directly from the DICOM data. Thus, the use of a complex auto-mapping can be avoided.

After transferring the local identification to the global identification 15 at the local medical imaging device 1, the local medical imaging device 1, in particular a reference module 22, receives the reference data 16 based on the global identification 15. In particular, the reference data 16 includes national reference values, institutional reference values and/or network specified reference values. Provided that a corresponding configuration value being used at the local medical imaging device exceeds the reference value 16 an alert notification 25 is generated by an alert module 24. By transferring 26 the alert notification to the operator of the local medical imaging device 1 the operator is informed about the mismatch between the used reference value and the reference value.

Furthermore it is provided that the results of analysing 5 the local identification and the results of the alert module 24 are transferred to a data collector module 30. These information are saved in the data collector module 30 together with the corresponding global identification 15. As a consequence, information saved in the data collector module 30 can be analysed by a analyse module 31, for example for further mapping processes or comparing different local medical imaging devices 1. Additionally the data collector module 30 can be used for benchmarking using a benchmark module 32.

In particular, it is provided that the benchmarking module 32 is configured for presenting benchmarking data set 41 to the local medical imaging device 1 or hospital 50 for comparing reference values of local medical imaging devices 1 of different hospitals 50 of the same type, location and/or area. In other words: the benchmarking module 32 is able to compare medical imaging devices 1 being comparable based on one or several classification values, such as a type of the hospital, a region and/or area the hospital is located in. Preferably, it is possible to select or to choose the classification values for calculating different benchmarking data sets at the local medical imaging device.

Preferably, it is provided that in a preparation step the local medical imaging device 1 or hospital 50 is registered by assigning an identifier to the hospital 50. For example, the classification values of the hospital 50 are saved together with the identifier to a memory during the registration 60, for example at the server. As a result, the server or the cloud can rely on the classification values for calculating a benchmarking data set 41. Preferably, the benchmarking data set 41 comprises a min-value, a max-value, a 25%-value, a 75% value, a mean value and/or a median value of reference values for different classification values, preferably defined by the registering 60 the hospital 50. Further, it is provided that the benchmarking data set 41 is generated monthly by a server 40 for calculating benchmarking data sets be relying on the data base.

For example,
a global benchmarking data set 41 or
a benchmarking data set 41 based on one classification value or based on a set of classification values is calculated. This calculated benchmarking data set 41 can be provided to the local medical imaging device 1 or hospital 50. Thus, each registered hospital 50 has immediately access to the preferred benchmarking data set 41.

Furthermore, incorporating 8 the global identification into the medical imaging device is provided, in particular such that the medical imaging device 1 can use the incorporated global identification 15 for labelling the medical imaging process, for example by incorporating the global identification into DICOM object, in particular for each modality. As consequence, it is advantageously possible to perform the labelling without mapping 21, in particular the auto-mapping mechanism.

Figure 2:
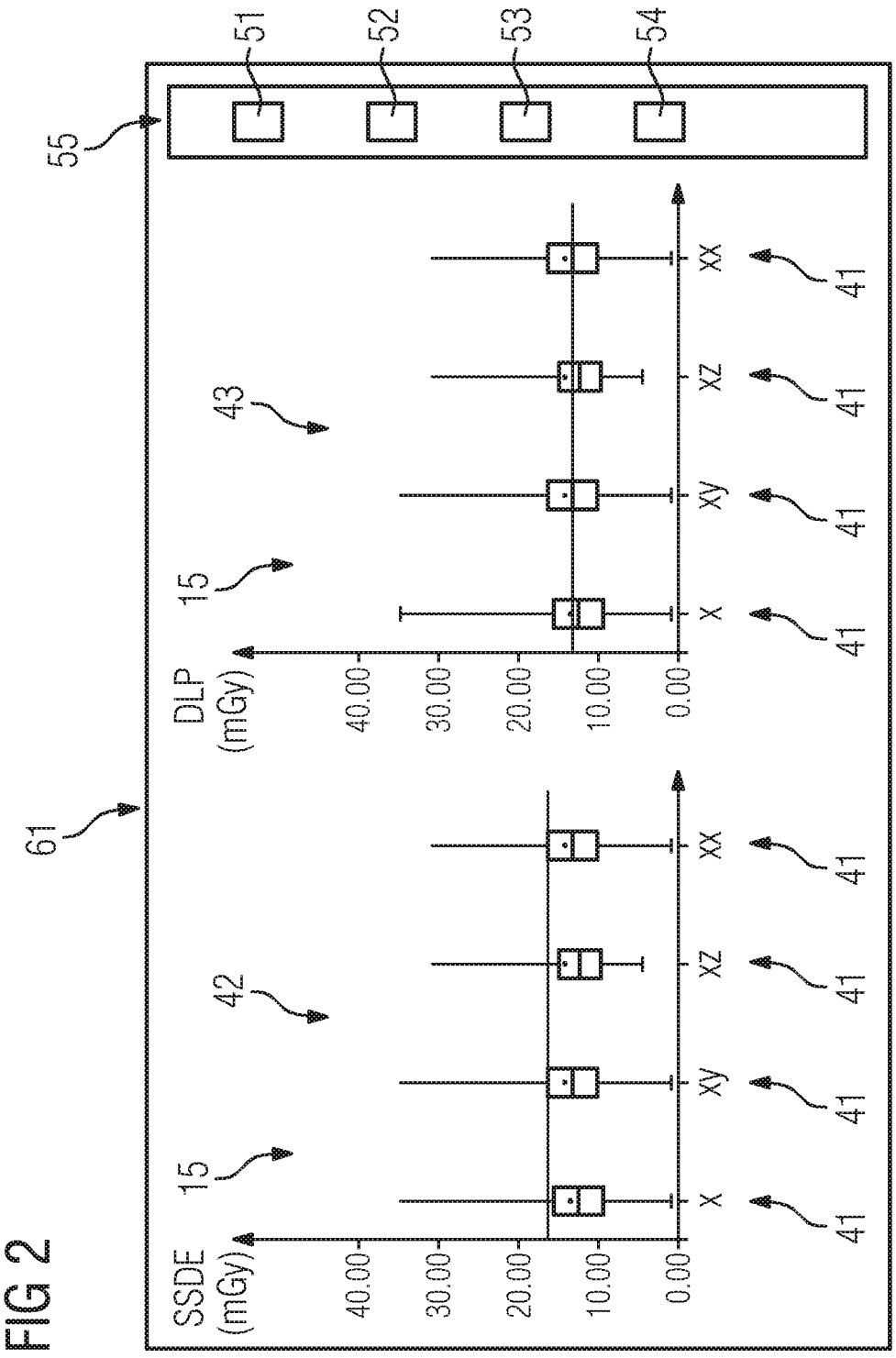
FIG. 2 shows a presentation of a benchmarking data set according to an embodiment of the present invention.

In FIG. 2 a presentation of a benchmarking data set 41 according to an example embodiment of the present invention is shown. For example, such a benchmarking data set 41 is provided to an operator on a screen such as a display of a workstation, of a tablet or a smartphone, preferably in form of a boxplot. In particular, the benchmarking data set 41 is presented in form of a boxplot and benchmarking data sets 41 for different classification values are displayed next to each other. Moreover, such an illustration of the results is available as well to show the evaluation with respect to the data available at the server, in particular at the cloud, without applying the restrictive classification values. Finally, there is an evaluation showing the results of the hospital itself with its own values.

Furthermore, a control area 55 is displayed on the screen 61, wherein the user can chose a specific modality in a list of modalities 51. Furthermore the user can select one or more RADLEX body regions from a list of RADLEX body regions 52, one or more RADLEX protocols from a list of RADLEX protocols 53 and/or the patient age 54 (adult or pediatric). For selecting the modality an input unit is provided, wherein the input unit represents a human machine interface. Preferably, it is provided that the benchmarking data being presented on the screen depends on the KPI defined for the selected modality. In the displayed embodiment it is provided that the benchmarking data for a first KPI 42, such a SSDE-value, and a second KPI 43, such as a DLP-value, are presented next to each other.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for comparing reference values in medical imaging processes of different medical imaging devices, wherein a data base is available to a plurality of spatially separated local medical imaging devices, the method comprising:
providing, by a configuration module, the data base with reference values, wherein each reference value of the reference values of the data base is assigned to a defined global identification specifying a medical imaging process of the medical imaging processes;
creating a label for the medical imaging process at at least one of a local medical imaging device or a local workstation, by using the defined global identification specifying the medical imaging process;
providing, by a mapping module, a mapping assigning a local identification to the defined global identification for supporting the creating of the label for the medical imaging process, wherein the data base is available to the plurality of spatial separated local medical imaging devices; and
providing a graphical user interface configured to receive input of at least one among a set of benchmarking parameters, the at least one of the set of benchmarking parameters including at least one of a modality, a body region, a protocol or a patient age, and the input including a selection of a first interface area of the graphical user interface,
wherein a benchmarking data set is created for a subset of local medical imaging devices by,
assigning a classification value to each respective local medical imaging device among the subset of local medical imaging devices, and
creating a benchmarking data set based on the classification value and the at least one among the set of benchmarking parameters input via the graphical user interface.

2. The method of claim 1, wherein the benchmarking data set is created on demand or after a defined period of time.

3. The method of claim 2, wherein the mapping is provided by a manual mapping mechanism when an auto-mapping mechanism fails.

4. The method of claim 1, wherein the mapping is provided by a manual mapping mechanism when an auto-mapping mechanism fails.

5. The method of claim 4, wherein the auto-mapping mechanism is performed by an artificial network.

6. The method of claim 1, wherein in a preparation step, an identifier is assigned to the local medical imaging device.

7. The method of claim 1, wherein the mapping that assigns the local identification to the defined global identification is visualized to an operator.

8. The method of claim 1, wherein the defined global identification is included as information into a DICOM-object.

9. The method of claim 1, wherein the data base of reference values is stored on a server.

10. The method of claim 1, further comprising:
generating an alarm via an alert module, upon a configuration value being used that exceeds a reference value of the reference values.

11. The method of claim 1, wherein several references values are provided based upon one of the reference values, via a configuration module.

12. The method of claim 1, wherein the creating of a label for the medical imaging process is at a workstation related to the local medical imaging device.

13. The method of claim 1, wherein the plurality of spatial separated local medical imaging devices include local medical imaging devices, located at different hospitals.

14. The method according to claim 1, wherein
the subset of local medical imaging devices are local medical imaging devices of different hospitals, and
the assigning assigns the classification value to the hospital of the medical imaging device.

15. The method of claim 14, wherein the benchmarking data set is created on demand or after a defined period of time.

16. The method of claim 1, wherein in a preparation step, an identifier is assigned to a hospital of the local medical imaging device.

17. The method of claim 1, wherein the benchmarking data set is visualized to an operator.

18. The method of claim 1, wherein the method further comprises:
generating an alert notification in response to determining a particular medical imaging process is configured to use a value exceeding a corresponding reference value among the reference values; and
outputting the alert notification.

19. The method of claim 1, wherein each of the reference values represents a critical threshold.

20. The method of claim 1, further comprising:
generating another graphical user interface presenting the benchmarking data set next to another benchmarking data set, the benchmarking data set being based on a plurality of local reference values of the plurality of spatially separated local medical imaging devices, and the other benchmarking data set being based on another classification value; and
outputting the other graphical user interface to a display.

21. The method of claim 1, wherein a first reference value among the reference values is determined based on a second reference value among the reference values.

22. The method of claim 21, wherein the first reference value corresponds to an organ and the second reference value corresponds to an imaging modality.

23. The method of claim 1, further comprising:
converting a first local identification for a first medical imaging process to the defined global identification for the first medical imaging process, the first local identification being received with a first reference value from a first local medical imaging device or a first local workstation;
storing the defined global identification for the first medical imaging process in association with the first reference value in the data base, the first reference value being included among the reference values; and
transmitting the defined global identification for the first medical imaging process and the first reference value to a second local medical imaging device or a second local workstation.

24. The method of claim 1, wherein the creating the benchmarking data set creates the benchmarking data set based on at least two among the set of benchmarking parameters, the at least two among the set of benchmarking parameters being determined based on a selection of the first interface area and a second interface area of the graphical user interface.

25. The method of claim 1, wherein the graphical user interface includes a control area having a set of interface areas, each respective interface area among the set of interface areas corresponding to a different benchmarking parameter among the set of benchmarking parameters.

26. A system, comprising:
at least one of a local medical imaging device or a local workstation, wherein a data base is available to several spatially separated local medical imaging devices, and wherein the system is configured to
provide, by a configuration module, the data base with reference values, wherein each reference value of the reference values of the data base is assigned to a defined global identification specifying a medical imaging process of the medical imaging processes,
create a label for the medical imaging process at at least one of a local medical imaging device or a local workstation, by using the defined global identification specifying the medical imaging process,
provide, by a mapping module, a mapping adapted to assign a local identification to the defined global identification for supporting creation of the label for the medical imaging process, and
provide a graphical user interface configured to receive input of at least one among a set of benchmarking parameters, the at least one of the set of benchmarking parameters including at least one of a modality, a body region, a protocol or a patient age, and the input including a selection of a first interface area of the graphical user interface,
wherein a benchmarking data set is created for a subset of local medical imaging devices based on the at least one among the set of benchmarking parameters input via the graphical user interface.

27. The system of claim 26, wherein each of the reference values corresponds to a magnitude of radiation or a duration of the radiation.

28. The system of claim 26, wherein the system is configured to:
create the benchmarking data set for the subset of local medical imaging devices by,
assigning a classification value to each respective local medical imaging device among the subset of local medical imaging devices, and
creating a benchmarking data set based on the classification value and the at least one among the set of benchmarking parameters input via the graphical user interface.

29. A non-transitory computer-readable medium storing program elements, readable and executable by a computer unit, that when executed by the computer unit, cause the computer unit to perform a method for comparing reference values in medical imaging processes of different medical imaging devices, wherein a data base is available to a plurality of spatially separated local medical imaging devices, the method comprising:
providing, by a configuration module, the data base with reference values, wherein each reference value of the reference values of the data base is assigned to a defined global identification specifying a medical imaging process of the medical imaging processes;
creating a label for the medical imaging process at at least one of a local medical imaging device or a local workstation, by using the defined global identification specifying the medical imaging process;
providing, by a mapping module, a mapping assigning a local identification to the defined global identification for supporting the creating of the label for the medical imaging process, wherein the data base is available to the plurality of spatially separated local medical imaging devices; and providing a graphical user interface configured to receive input of at least one among a set of benchmarking parameters, the at least one of the set of benchmarking parameters including at least one of a modality, a body region, a protocol or a patient age, and the input including a selection of a first interface area of the graphical user interface, wherein a benchmarking data set is created for a subset of local medical imaging devices by, assigning a classification value to each respective local medical imaging device among the subset of local medical imaging devices, and creating a benchmarking data set based on the classification value and the at least one among the set of benchmarking parameters input via the graphical user interface.

* * * * *